US00PP23031P2

(12) United States Plant Patent
Byrne

(10) Patent No.: US PP23,031 P2
(45) Date of Patent: Sep. 11, 2012

(54) POINSETTIA PLANT NAMED 'PER14606'

(50) Latin Name: ***Euphorbia pulcherrima* Willd.**
Varietal Denomination: PER14606

(75) Inventor: Peter Byrne, Stratford-upon-Avon (GB)

(73) Assignee: The Paul Ecke Ranch, Encinitas, CA (US)

( * ) Notice: Subject to any disclaimer, the term of this patent is extended or adjusted under 35 U.S.C. 154(b) by 245 days.

(21) Appl. No.: 12/802,242

(22) Filed: Jun. 1, 2010

(51) Int. Cl.
*A01H 5/00* (2006.01)

(52) U.S. Cl. ..... Plt./307

(58) Field of Classification Search ..... Plt./307
See application file for complete search history.

(56) References Cited

U.S. PATENT DOCUMENTS

| | | | | |
|---|---|---|---|---|
| PP11,889 | P2 * | 5/2001 | Fruehwirth | Plt./307 |
| PP13,838 | P2 * | 5/2003 | Fruehwirth | Plt./307 |
| PP18,627 | P2 * | 3/2008 | Dummen | Plt./307 |

* cited by examiner

*Primary Examiner* — Wendy C Haas
(74) *Attorney, Agent, or Firm* — C. A. Whealy

(57) ABSTRACT

A new and distinct cultivar of Poinsettia plant named 'PER14606', characterized by its uniform, upright and mounded plant habit; moderately vigorous growth habit; freely branching habit; green and pale yellow variegated leaves; mid-season flowering response; large inflorescences with red-colored flower bracts; and good post-production longevity.

1 Drawing Sheet

Botanical designation: *Euphorbia pulcherrima* Willd.
Cultivar denomination: 'PER14606'.

BACKGROUND OF THE INVENTION

The present invention relates to a new and distinct cultivar of Poinsettia plant, botanically known as *Euphorbia pulcherrima* Willd., and hereinafter referred to by the name 'PER14606'.

The new Poinsettia plant is a naturally-occurring whole plant mutation of *Euphorbia pulcherrima* Willd. 'Eckakeem', disclosed in U.S. Plant Pat. No. 13,838. The new Poinsettia plant was discovered and selected by the Inventor as a flowering plant from within a population of plants of 'Eckakeem' in a controlled greenhouse environment in Stratford-upon-Avon, Warwickshire, United Kingdom in August, 2005.

Asexual reproduction of the new Poinsettia plant by terminal vegetative cuttings in a controlled greenhouse environment in Encinitas, Calif. since June, 2006, has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER14606'. These characteristics in combination distinguish 'PER14606' as a new and distinct cultivar of Poinsettia plant:

1.. Uniform, upright and mounded plant habit.
2. Moderately vigorous growth habit.

3. Freely branching habit.
4. Green and pale yellow variegated leaves.
5. Mid-season flowering response; under natural season conditions, plants flower in about nine weeks in Southern California.
6. Large inflorescences with red-colored flower bracts.
7. Good post-production longevity.

In side-by-side comparisons conducted in Encinitas, Calif., plants of the new Poinsettia differed primarily from plants of the parent, 'Eckakeem', in the following characteristics:

1. Plants of the new Poinsettia were more compact than plants of 'Eckakeem'.
2. Leaves of plants of the new Poinsettia were green and pale yellow variegated whereas leaves of plants of 'Eckakeem' were dark green in color.

Plants of the new Poinsettia can be compared to plants of the *Euphorbia pulcherrima* Willd. 'Eckansley', disclosed in U.S. Plant Pat. No. 11,889. In side-by-side comparisons conducted in Encinitas, Calif., plants of the new Poinsettia differed primarily from plants of 'Eckansley' in the following characteristics:

1. Plants of the new Poinsettia were more vigorous than and not as compact as plants of 'Eckansley'.
2. Plants of the new Poinsettia were more freely branching than plants of 'Eckansley'.
3. Plants of the new Poinsettia had stronger lateral branches than plants of 'Eckansley'.
4. The leaf variegation contrast of plants of the new Poinsettia was greater than the leaf variegation contrast of plants of 'Eckansley'.

BRIEF DESCRIPTION OF THE PHOTOGRAPHS

The accompanying photographs illustrate the overall appearance of the new Poinsettia plant. The photographs show the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER14606' grown in a container.

The photograph at the top of the sheet is a close-up view of a typical flowering plant of 'PER14606'.

DETAILED BOTANICAL DESCRIPTION

Plants used in the aforementioned photographs and in the following description describe plants grown in during the winter in 15-cm containers in a polyethylene-covered greenhouse in Encinitas, Calif. and under natural season conditions and cultural practices which approximate those generally used in commercial Poinsettia production. During the production of the plants, day temperatures averaged 25° C., night averaged 17° C. and light levels were about 4,000 foot-candles. Measurements and numerical values represent averages for typical flowering plants. Plants were pinched one time and were 18 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER14606'.

Parentage: Naturally-occurring whole plant mutation of *Euphorbia pulcherrima* Willd. 'Eckakeem', disclosed in U.S. Plant Pat. No. 13,838.

Propagation:

*Type*.—Terminal vegetative cuttings.

*Time to initiate roots*.—About seven to ten days at 20° C. night temperature.

*Time to produce a rooted young plant*.—About four weeks at 20° C. night temperature.

*Root description*.—Fibrous; white in color.

Plant description:

*Plant habit and form*.—Uniform, upright and mounded plant habit; narrow inverted triangle; large inflorescences positioned above the foliar plane; moderately vigorous growth habit.

*Plant height*.—About 27.5 cm.

*Plant diameter or spread*.—About 49 cm.

*Lateral branch description*.—Quantity: Freely branching habit, about seven to eight lateral branches develop after pinching. Length: About 26 cm. Diameter: About 6 mm. Internode length: About 2.2 cm. Strength: Strong. Texture: Smooth, glabrous. Color: Close to 146A.

*Foliage description*.—Arrangement: Alternate, simple. Aspect: Flat. Length: About 10.8 cm. Width: About 7.6 cm. Shape: Elliptical with three shallow irregular lobes. Apex: Acuminate. Base: Attenuate. Margin: Entire with three shallow irregular lobes. Venation pattern: Pinnate, arcuate. Texture, upper surface: Sparsely pubescent. Texture, lower surface: Pubescent. Color: Developing leaves, upper surface: Centers, close to 148A; towards the margins, irregular sectors, close to 6D. Developing leaves, lower surface: Centers, close to 147B; towards the margins, irregular sectors, close to 4C to 4D. Fully expanded leaves, upper surface: Centers, close to 148A and 147C; towards the margins, irregular sectors, close to 4C to 4D; venation, close to 185B to 185C. Fully expanded leaves, lower surface: Centers, close to 147B; towards the margins, irregular sectors, close to 4C to 4D; venation, close to 185C. Petiole: Length: About 7.5 cm to 8.5 cm. Diameter: About 3 mm. Texture, upper surface: Smooth, glabrous. Texture, lower surface: Sparsely pubescent. Color, upper surface: Close to 187C. Color, lower surface: Close to 187D.

Inflorescence description:

*Inflorescence type and habit*.—Inflorescences are compound corymbs of cyathia with colored flower bracts subtending the cyathia; inflorescences positioned above the foliar plane.

*Quantity of inflorescence*.—One inflorescence develops per lateral branch.

*Fragrance*.—Not detected.

*Natural flowering season*.—Plants typically flower during the autumn and winter in Southern California; inflorescence initiation and development can also be induced under artificial long nyctoperiod/short photoperiod conditions; mid-season flowering habit, plants flower about nine weeks when grown under natural season conditions in Southern California.

*Post-production longevity*.—Good post-production longevity; plants of the new Poinsettia maintain good substance and flower bract color for about four weeks under interior conditions; inflorescences persistent.

*Inflorescence size*.—Diameter: About 30 cm. Height (depth): About 7 cm.

*Flower bracts*.—Quantity per inflorescence: About 24. Length, largest bracts: About 12.5 cm. Width, largest bracts: About 8.8 cm. Shape: Elliptical. Apex: Acuminate. Base: Attenuate. Margin: Entire; outer bracts, somewhat irregular. Texture, upper and lower surfaces: Smooth, glabrous. Aspect: Flat to slightly upright; apices of outer bracts slightly droopy. Venation pattern: Pinnate, arcuate. Color: Developing or transitional bracts, upper surface: Centers, close to 147B; margins, close to 47A. Developing or transitional bracts, lower surface: Centers, close to 147B; towards the margins, close to 59D. Fully expanded bracts, upper surface: Close to 53C; venation, close to 53C; color does not fade with development. Fully expanded bracts, lower surface: More grey than 59D; venation, more grey than 59D; color does not fade with development. Bract petiole: Length: About 4.3 cm. Diameter: About 2 mm. Texture, upper and lower surfaces: Smooth, glabrous. Color, upper and lower surfaces: Close to 53B.

*Cyathia*.—Quantity per corymb: About eleven or twelve. Length: About 1 cm. Width: About 6 mm. Shape: Ovoid. Color, immature and mature: Close to 145A.

*Nectaries*.—Quantity per cyathium: One. Length: About 5 mm. Width: About 3 mm. Shape: Elliptical to ovoid. Color: Close to 14B.

*Peduncles*.—Length: About 2 mm. Diameter: About 2.5 mm. Strength: Strong. Aspect: Mostly upright. Texture: Smooth, glabrous. Color: Close to 145A.

*Reproductive organs*.—Stamens: Quantity per cyathium: About eight. Filament length: About 3 mm. Filament color: Close to 46A. Anther shape: Oval; bi-lobed. Anther length: About 1 mm. Anther color:

Close to 59A. Amount of pollen: Scarce. Pollen color: Close to 7A. Pistils: Plants of the new Poinsettia do not develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15.5° C. to about 29° C.

It is claimed:

1. A new and distinct Poinsettia plant named 'PER14606' as illustrated and described.

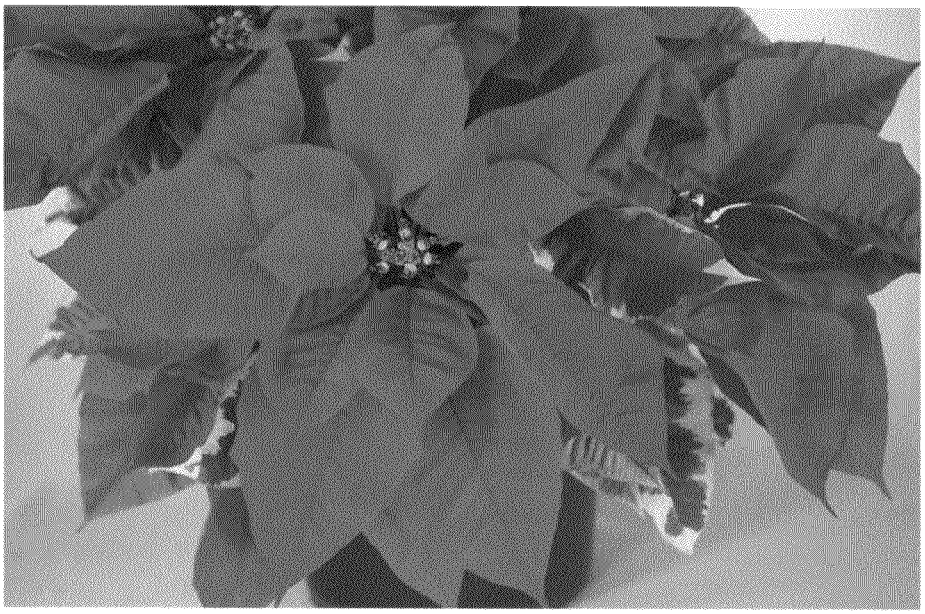
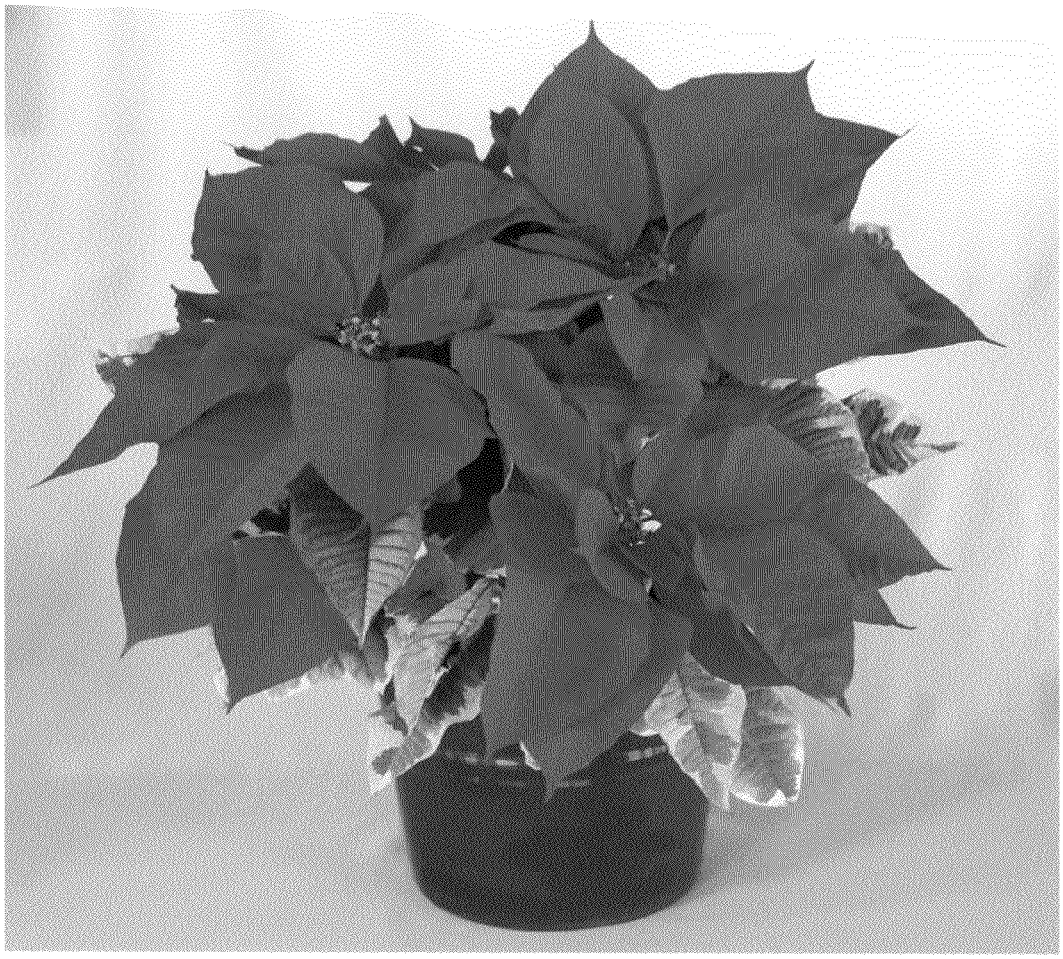

* * * * *